(12) United States Patent
Deshmukh

(10) Patent No.: US 8,320,987 B2
(45) Date of Patent: Nov. 27, 2012

(54) ELECTRIC POTENTIAL MAPPING AND ELECTRODE ATTACHMENT DEVICE WITH CONTINUOUS ELECTRIC SIGNAL MONITORING AND METHOD

(76) Inventor: Pramod M. Deshmukh, Sayre, PA (US)

( * ) Notice: Subject to any disclaimer, the term of this patent is extended or adjusted under 35 U.S.C. 154(b) by 367 days.

(21) Appl. No.: 12/838,468

(22) Filed: Jul. 18, 2010

(65) Prior Publication Data

US 2012/0016227 A1    Jan. 19, 2012

(51) Int. Cl.
*A61B 5/042* (2006.01)
(52) U.S. Cl. .............. 600/372; 600/508; 600/118
(58) Field of Classification Search .......... 600/372, 600/508, 118
See application file for complete search history.

(56) References Cited

U.S. PATENT DOCUMENTS

| 5,687,737 A * | 11/1997 | Branham et al. ............ 600/523 |
| 2009/0209950 A1 * | 8/2009 | Starksen ..................... 606/21 |

* cited by examiner

*Primary Examiner* — Carl H Layno
*Assistant Examiner* — Natasha Patel
(74) *Attorney, Agent, or Firm* — Craig A. Simmermon

(57) ABSTRACT

Electric potential mapping and electrode attachment device comprises: a main cylinder; a center piece having a center piece passage for receiving a catheter with its electrode running from a center piece inlet to a center piece outlet; a cylinder cap for closing main cylinder; a second cylinder which fits inside of and is allowed to rotate relative to main cylinder; and at least two electromechanical connections used to connect the device to at least two connectors on an electrode lead, where the device facilitates rotation and movement of each connector relative to the other while retaining continuous electrical connection with heart tissue or other body cavity tissue. The device offers continuous recording of electrical potentials of a body cavity during full rotation of collars, connectors, or connections on a laparoscopic device during HIS bundle mapping, pacemaker electrode anchoring, post anchoring, pacemaker programming, and afterwards.

10 Claims, 12 Drawing Sheets

ELECTRIC POTENTIAL MAPPING AND ELECTRODE ATTACHMENT DEVICE WITH CONTINUOUS ELECTRIC SIGNAL MONITORING AND METHOD

BACKGROUND OF THE INVENTION

1. Field of the Invention

The present invention relates to a novel electric potential mapping and electrode attachment device used to locate and map the HIS bundle electrical impulse section of the heart or any other cavity within the body and produce a high-quality electrocardiogram of the HIS bundle or other cavity with continuous electrical readings through cavity mapping, electrode attachment, final implantation into the patient, and programming of the pacemaker device.

2. Description of Related Art

The contractions of the atria and ventricles of a heart are synchronized for efficient pumping of blood through the body. An electrical impulse created by the sinus node is conducted to the ventricles by a specialized conduction system, referred to as the His bundle and His Purkinje system. The bundle of His, also known as the AV bundle or atrioventricular bundle, is a collection of heart muscle cells specialized for electrical conduction that transmits electrical impulses from the AV node (located between the atria and the ventricles) to the point of apex of the fascicular branches. The fascicular branches then lead to the Purkinje fibers which innervate the ventricles, causing the cardiac muscle of the ventricles to contract at a paced interval. The His bundle is responsible for rapid sequential multi-site activation of the ventricle which results in efficient simultaneous contraction of both heart ventricles.

At times, an external device, such as an artificial pacemaker, is connected to the heart for activation of the myocardium. The impulse is carried through a set of electric wires (leads) to the electrode placed on or in the heart. The most common position of these electrodes is the right ventricular apex. The electrical stimulus causes the heart muscle to contract. This can be seen in U.S. Pat. No. 5,902,324 "Bi-Atrial and Bi-Ventricular Sequential Cardiac Pacing Systems" Thompson et al. issued May 11, 1999, (Thompson).

It has been determined that stimulation and pacing are more efficient if the His bundle system is stimulated instead of the heart muscle. This has been described in "Permanent, Direct His-Bundle Pacing—A Novel Approach to Cardiac Pacing in Patients With Normal His-Purkinje Activation", Pramod Deshmukh, MD, David A. Casavant, MS, Mary Romanyshyn, CRNP, Kathleen Anderson, BSN, Oct. 1, 1999, cardiology Div., Robert Packard Hospital, Sayre, Pa. and Medtronic, inc. Minneapolis, Minn., © 2000 American Heart institute, (Deshmukh). This paper indicated that the right ventricular (RV) apical pacing caused abnormal contraction of the ventricles had disadvantageous effects on cardiac efficiency. RV pacing has also been associated with changes that cause the left ventricular function to deteriorate, "Long-Term His-Bundle Pacing and Cardiac Function" by Melvin M. Scheinman, MD, Leslie A. Saxon, MD, Dept. of Medicine, Univ. of California, San Francisco, © 2000 American Heart Association, Inc., (Scheinman). Scheinman supports and reiterates the findings of Deshmukh.

The process of mapping the HIS bundle and attaching the electrode to a precise location in the HIS bundle is currently an extremely difficult surgical procedure because the HIS bundle is very small and is located inside of a small heart chamber in blind corner location that is very difficult to get to laproscopically. This can be seen in U.S. Pat. No. 6,937,897 B2 "Electrode for HIS Bundle Stimulation", Min et al. issued Aug. 30, 2005, The location and attachment process can become more difficult since the heart is beating and the location of the HIS bundle changes throughout the beating cycle. The heart 'torques' when it beats so it translates and rotates as it expands and contracts. In addition, the current means of accessing the HIS bundle is by passing a catheter through the superior vena cava into the atrium and placing it against the atrium wall, so all positioning must be done remotely by manipulating a catheter from outside of the patient.

Note that this invention is very suitable for application and mapping of other body cavities. The HIS bundle is very small and is located in a very hard to reach area. Because of the high degree of control required to effectively map this cavity, the device may be easily used to map practically any other body cavity in humans or animals.

Pacemaker electrodes are attached to heart tissue by screw means. A screw is a helix or a corkscrew-shaped appendage attached to the distal end of the electrode, with its longitudinal axis normal to the distal outer surface of the electrode, where the helix is used to literally screw into heart tissue or otherwise attach or seat the distal outer surface of the electrode onto heart tissue at a precise point. Electrodes typically use a fixed screw or a rotational screw design. With fixed screw electrodes, the helix is fixed onto the distal outer surface of the electrode. Thus, the whole electrode must be rotated to rotate the helix and attach the electrode to the heart. With rotational screw electrodes, the helix may be rotated in isolation, without also rotating of the electrode. With rotational screw, the helix is fixed to a holder, where the holder may be rotated, causing the helix to rotate and extent distally from the distal outer surface of the electrode, thereby extending the screw from such and attaching to heart tissue. The distal surface of the electrode has a hole or aperture from which the helix extends and retracts.

Mapping is the process of positioning the electrode, recording an electrical potential reading, repositioning the electrode, recording another electrical signal, and repeating until an accurate enough map or sufficient amount of electrical readings is taken by the surgeon to render an electrical topography of the heart chamber or otherwise enough information to determine the exact best position on the His bundle to attach the electrode in order to stimulate the simultaneous contraction of both ventricles to achieve maximum pumping efficiency. The electrical potential reading used in the mapping process is the electric potential difference between the electrode collar and the electrode helix, as set forth in Deshmukh. The electrode collar is located on the distal outer surface of the electrode. The electrode collar is typically the outer ring on the distal outer surface of the electrode. In the case of rotational screw electrodes, typically, the helix extends from the center of the ring of electrode collar.

With prior art methods and devices, after the surgeon determines the precise optimum attachment point, he must disconnect one or both electrical signals/readings in order to begin and complete the rotating of the electrode or helix. At this point, the electrode may move slightly off-center, in any direction, from its precise location. A fraction of a millimeter shift could substantially change electrical readings.

Such mislocations are typically discovered after attachment, when the surgeon re-connects electrical signals to see that the electrical readings have changed. At this point, the surgeon must: disconnect electrical signals, retract the electrode or helix, reconnect electrical signals, remap, relocated electrode, disconnect electrical signals, reattach electrode to heart, reconnect electrical signals, and recheck electrical signals, perhaps only to repeat this procedure over and over again. This could theoretically lead to an endless cycle or infinite loop of mislocations.

To solve this problem, this invention provides continuous electrical signal monitoring of the heart as the electrode is moved within the heart and rotated for attachment means into heart tissue. Thus, if the electrode were to move off-center from the precise location determined by electrical signal readings, then the surgeon would immediately know, discontinue attachment, unscrew the electrode or helix, and make adjustments or otherwise relocate to offset the effect, and begin attachment again. Electrical signals are also continuously monitored after attachment. The surgeon can be certain of accurate and precise electrode placement. The method of attachment disclosed here allows more exact control and placement of the electrode because of the superior amount of measurement data produced by electric potential mapping and electrode attachment device.

Additionally, electric potential mapping and electrode attachment device can provide a complete and uninterrupted electrocardiogram of the HIS bundle. The surgeon has continuous electric potential readings right up to final disconnection of the attachment device and attachment of the pacemaker control module for final insertion into the patient. This data is necessary as set forth in Deshmukh to program the pacemaker "to pace" the heart most efficiently. Electric potential mapping and electrode attachment device is first to provide such a cardiogram of the HIS bundle during rotation and attachment as well as before and after. This data better ensures that the pacemaker will be programmed to run in the most efficient fashion because the cardiogram used for input in the programming is more exact, without disconnection of electrical contacts, ending of one cardiogram, only to start a new one after electrode attachment. With the prior art, it would be possible to use a cardiogram generated from a different location, where the electrode move off-center slightly during attachment. This would yield improper programming of the pacemaker, so it would not pace the heart in the most efficient fashion.

BRIEF SUMMARY OF THE INVENTION

Electric potential mapping and electrode attachment device comprises: a main cylinder; a center piece having a center piece passage for receiving a catheter with its electrode running from a center piece net to a center piece outlet; a cylinder cap for closing main cylinder; a second cylinder which fits inside of and is allowed to rotate relative to main cylinder; and at least two electromechanical connections used to connect the device to at least two connectors on an electrode lead, where the device facilitates rotation and movement of each connector relative to the other while retaining continuous electrical connection with heart tissue or other body cavity tissue.

A laparoscopic device is attached to electric potential mapping and electrode attachment device. Electric potential mapping and electrode attachment device is used to better implant, locate, attach, and program the laparoscopic device and otherwise most efficiently implement the device into the patient. A laparoscopic device is a device that is inserted into a small incision, usually 0.5-⅕ cm, in the abdomen, and is used for minimally invasive surgery. A pacemaker electrode with attached wire lead is such a laparoscopic device. Any laparoscopic device may be mated with the invention. Invention is used to better locate, implant, attach and or program the laparoscopic device.

Electric potential mapping and electrode attachment device is capable of continuously recording electrical potentials of a heart cavity or other body cavity during full rotation of collars, connectors, or connections on the laparoscopic device.

Electric potential mapping and electrode attachment device is capable continuously recording electrical signals during HIS bundle mapping, pacemaker electrode anchoring, post anchoring, pacemaker programming, and afterwards.

Electric potential mapping and electrode attachment device is capable of continuously recording electrical potentials of any body cavity during manipulation and full rotation of the attached laparoscopic device.

Electric potential mapping and electrode attachment device is capable of receiving and holding a pacemaker lead inside of a catheter having an electrode at its distal end or other laparoscopic device.

Electric potential mapping and electrode attachment device can be used by the surgeon to precisely manipulate or position the electrode or other laparoscopic device in a heart chamber or other body cavity.

Electric potential mapping and electrode attachment device can be used by the surgeon to precisely manipulate or position any laparoscopic device in any body cavity.

It is an aspect of the invention to provide a positioning device to position and secure a cardiac pacemaker electrode to the HIS bundle section of a heart, which is located inside a small chamber of another chamber, while continuously recording relevant electrical potentials of the cavities.

It is an aspect of the invention to provide a means for securing the electrode and lead from a cardiac pacemaker in a precise location on the HIS bundle inside a heart chamber, at the exact location that yields maximum efficiency regarding timing and pacing of heart valves, while continuously recording relevant electrical potentials of the heart.

It is an aspect of the invention to provide a means for retaining continuous electrical signal connections with the electrode from mapping, electrode attachment, to pacemaker control unit programming, without interruption of the electrical signals.

It is an aspect of the invention to provide the ability for a surgeon to screw-in, rotate, or otherwise attach a cardiac pacemaker electrode to patient tissue with the same hand used to manipulate or position the electrode in a heart chamber while retaining continuous electrical signal connections and monitoring during such one handed rotation and manipulation, leaving the other hand free to position another medical device, operate a computer, or other interface.

DETAILED DESCRIPTION OF THE INVENTION

Figure 1:
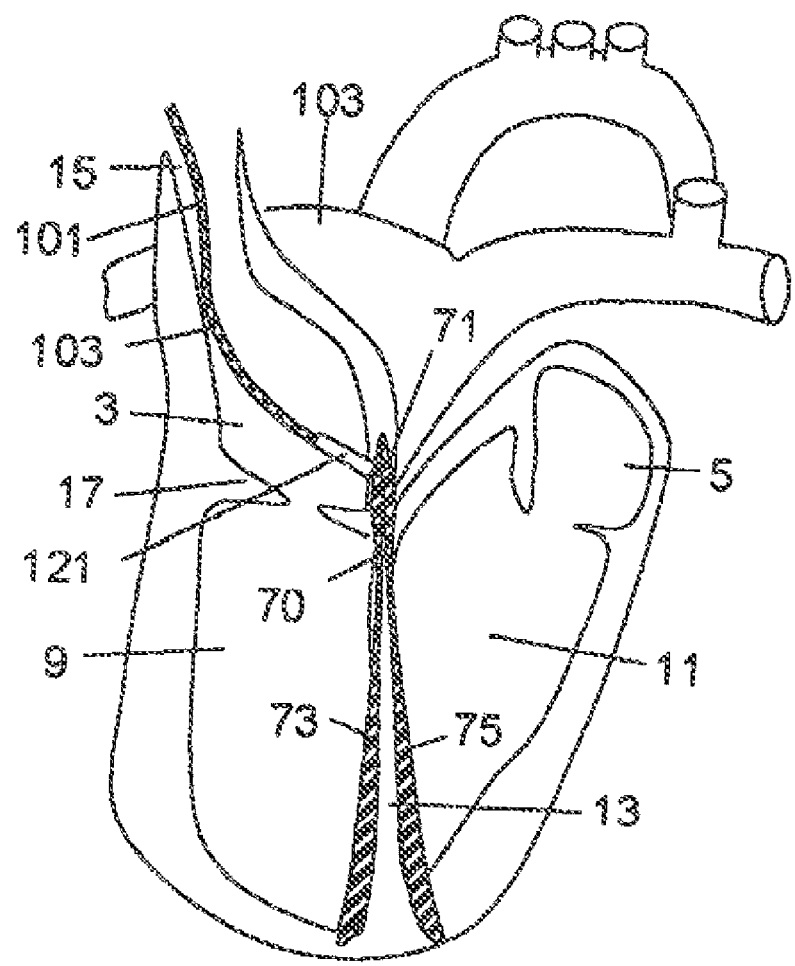
FIG. 1 is a schematic illustration of a cross section of a human heart showing a catheter stimulating the heart.
Figure 2:
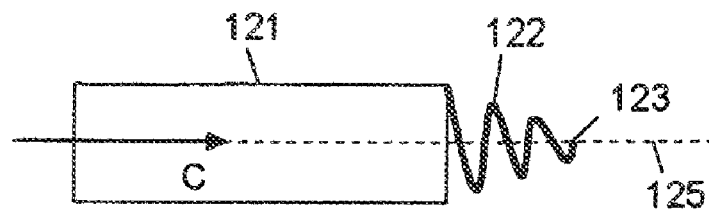
FIG. 2 is a side elevation view of a typical pacemaker electrode with corkscrew helix.

FIG. 1 is a schematic illustration of a cross section of a human heart showing a catheter stimulating the heart. Here the right and left atria 3, 5 and right and left ventricles 9, 11 are shown. An upper section atrial HIS bundle 71 of a His Perkinje nerve fiber bundle 70 (HIS bundle) is present in the wall of right atrium 3 which passes down a septum 13 to a right ventricle 9 and a left ventricle 11. In normal operation, electrical stimulation of the atrial HIS bundle 71 causes the atria 3, 5 to simultaneously contract passing blood through the tricuspid valve 17 and into the right ventricle 9. The signal moves slowly downward into the right HIS bundle branch 73 and the left HIS bundle branch 75 causing right and left: ventricles 9, 11, respectively, to begin to contract as the atria 3, 5 have just about completed their contraction. The delayed contraction of ventricles 9, 11 allows maximal ejection fraction of the heart and optimum pumping efficiency. When the timing is thrown off, by disease or other disorder, the efficiency drops considerably. This may be due to a non-conductive section of the HIS bundle. Thus, it is very important to correct contractions regarding improper timing. Usually, a cardiac pacemaker system is used to correct said contractions.

Cardiac pacemaker systems (pacemakers) typically comprise: a power/control unit (not depicted); at least one electrode 121; a wire lead 103; an electromechanical connector 131; and a stylet 141. Electrode 121 is permanently attached to one end of wire lead 103 and an electromechanical connector 131 is permanently attached to the other end of wire lead 103. Electrode 121 typically comprises an electrode collar 127 and a helix 122.

Figure 3:
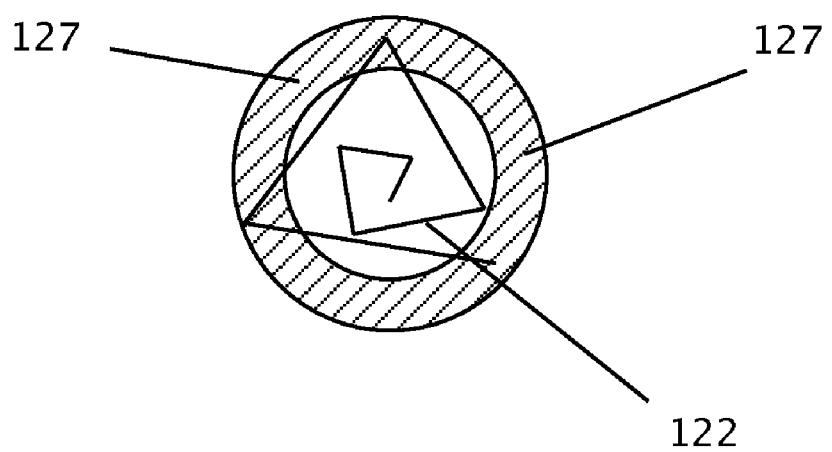
FIG. 3 is an end elevation view of the distal end of a typical pacemaker electrode with corkscrew helix.
Figure 4:
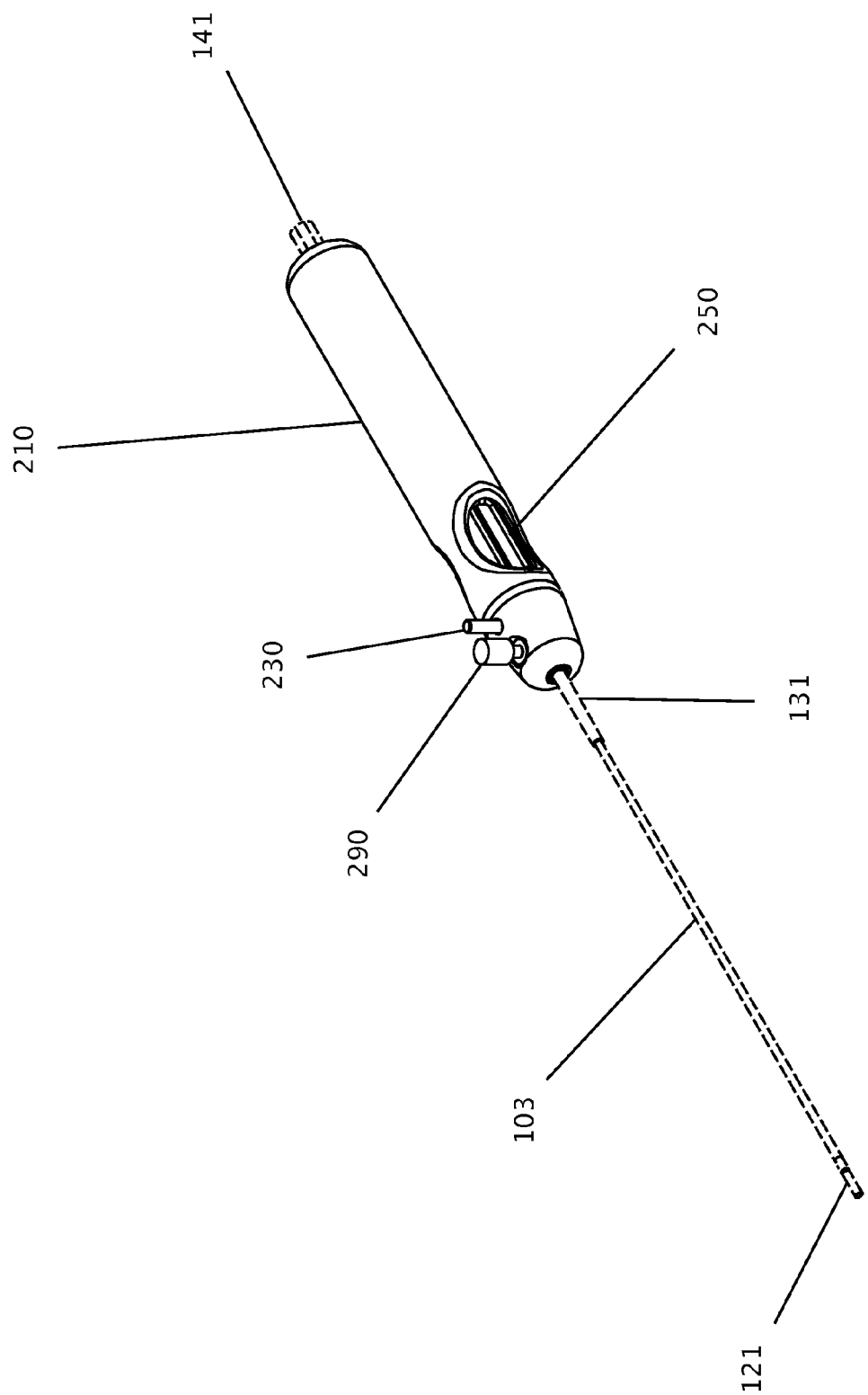
FIG. 4 is a top perspective view of electric potential mapping and electrode attachment device with both electrode and stylet inserted or attached.
Figure 5:
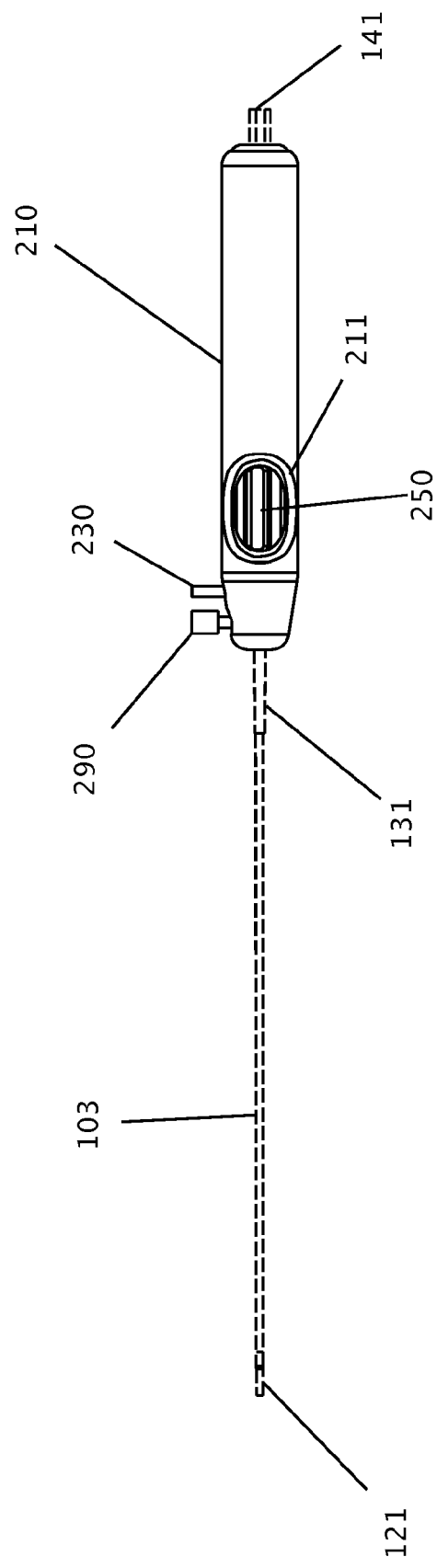
FIG. 5 is a side elevation view of electric potential mapping and electrode attachment device with both electrode and stylet inserted or attached.
Figure 6:
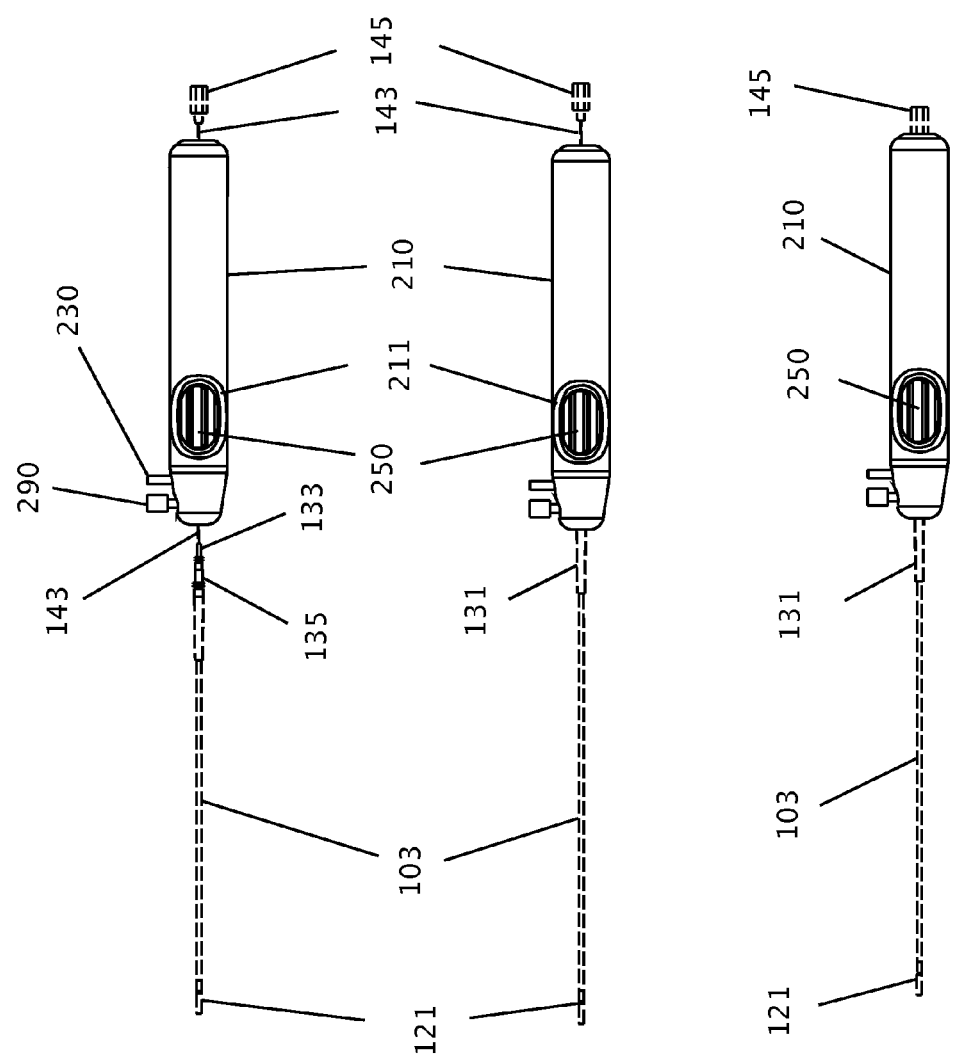
FIG. 6 has three side elevation views of electric potential mapping and electrode attachment device with both electrode and stylet just before and after insertion or attachment of each.
Figure 7:
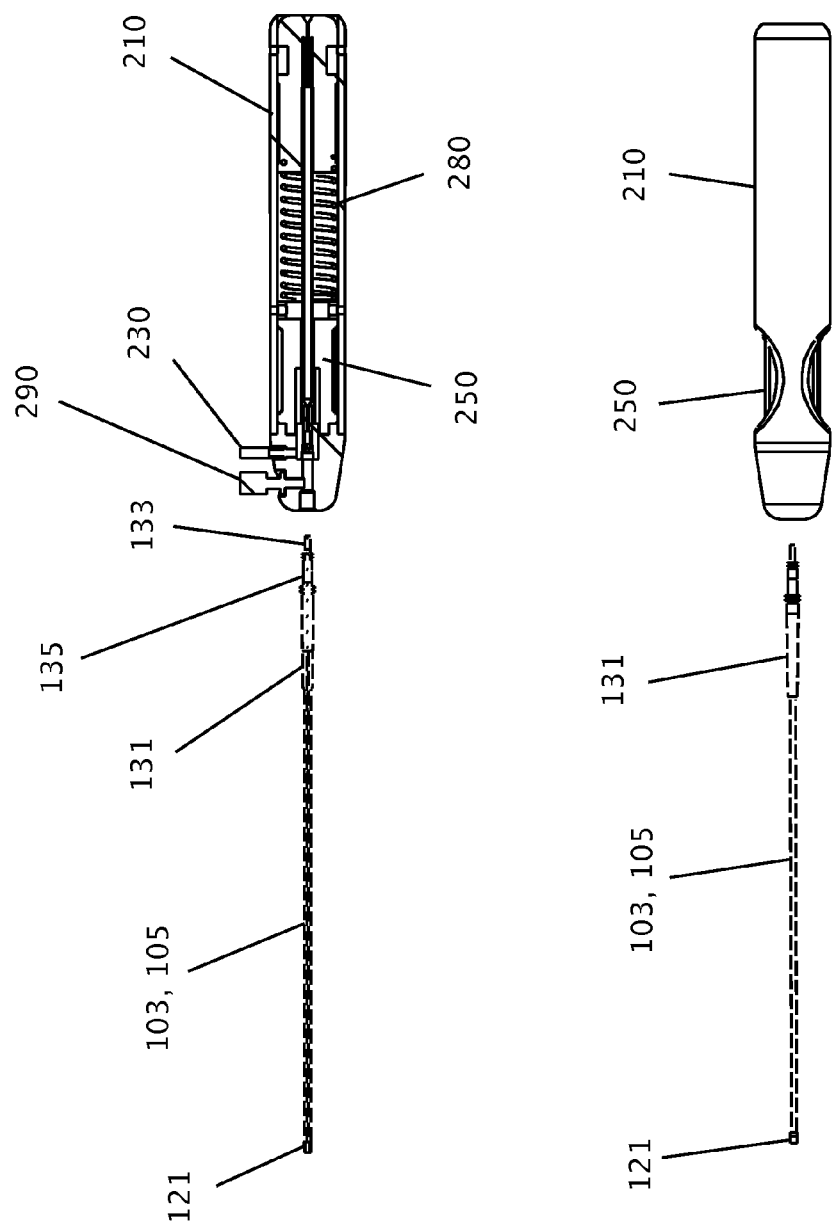
FIG. 7 is a cross sectional view of electric potential mapping and electrode attachment device with electrode just before attachment and a bottom plan view of electric potential mapping and electrode attachment device with electrode just before attachment.
Figure 8:
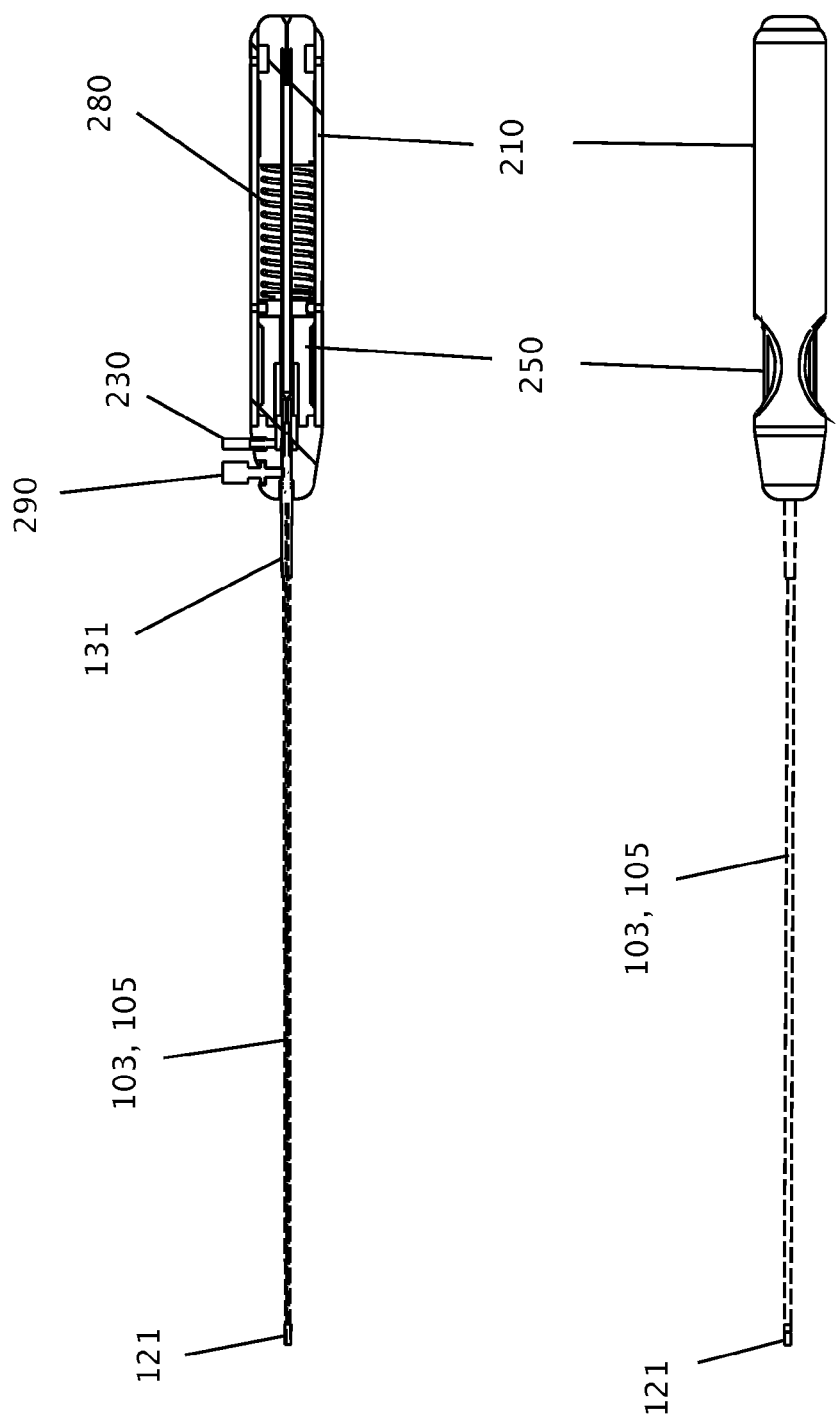
FIG. 8 is a cross sectional view of electric potential mapping and electrode attachment device with attached electrode and a bottom plan view of electric potential mapping and electrode attachment device with attached electrode.
Figure 9:
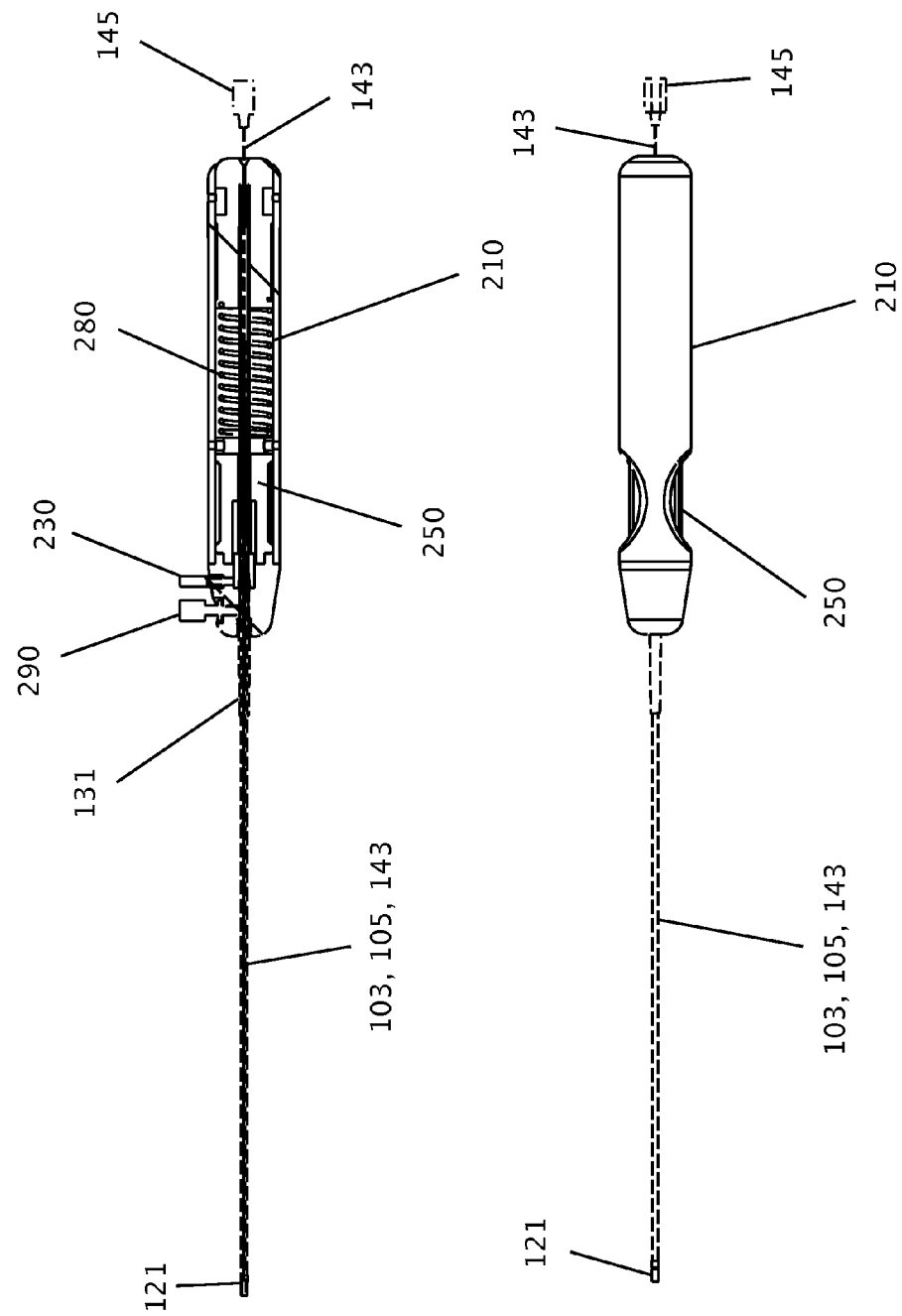
FIG. 9 is a cross sectional view of electric potential mapping and electrode attachment device with attached electrode and stylet and a bottom plan view of electric potential mapping and electrode attachment device with attached electrode and stylet.
Figure 10:
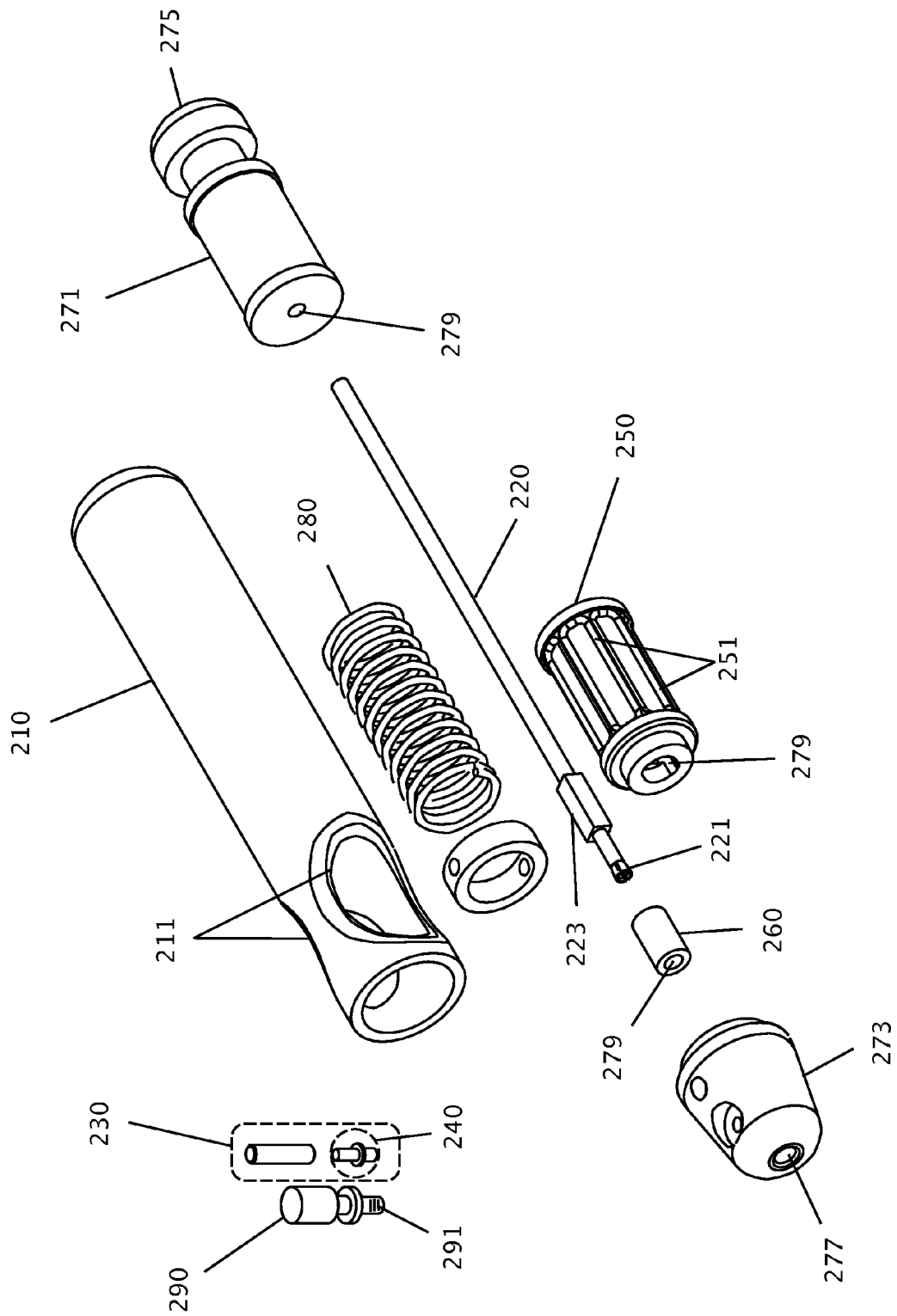
FIG. 10 is an exploded view of electric potential mapping and electrode attachment device.
Figure 11:
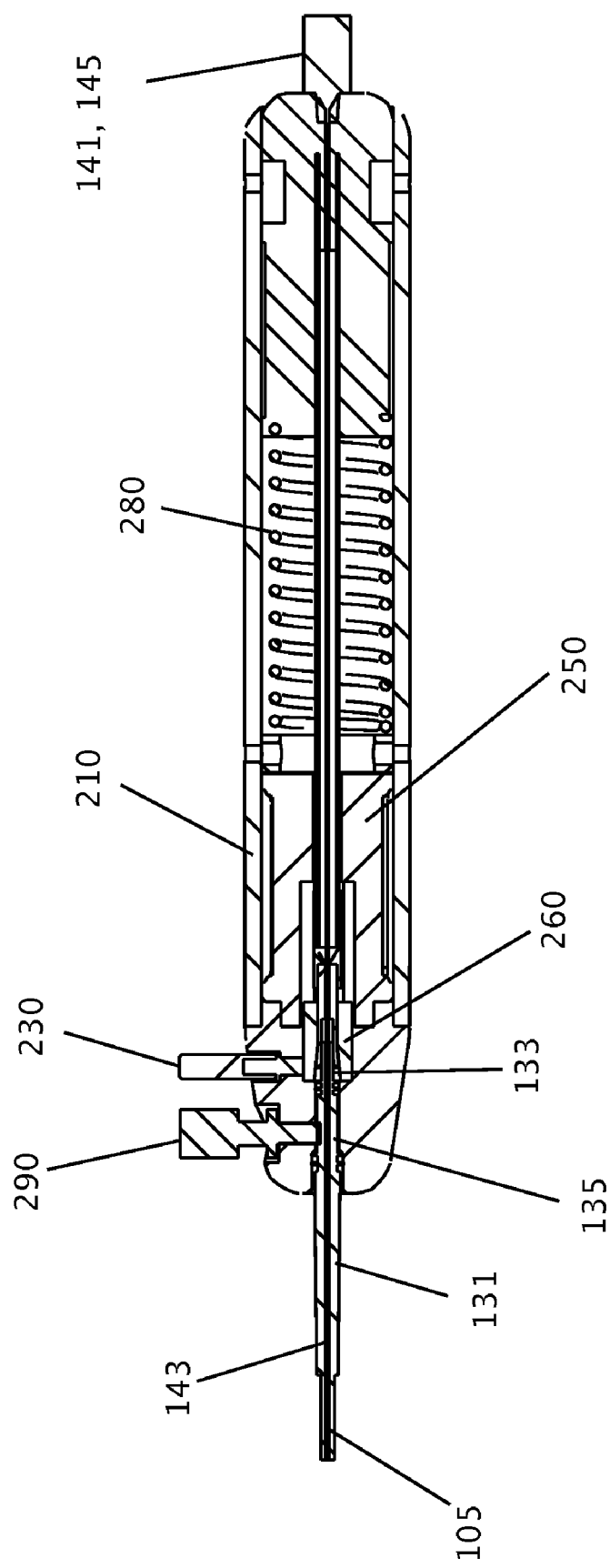
FIG. 11 is a blow-up of a cross sectional view of electric potential mapping and electrode attachment device with attached electrode and stylet.
Figure 12:
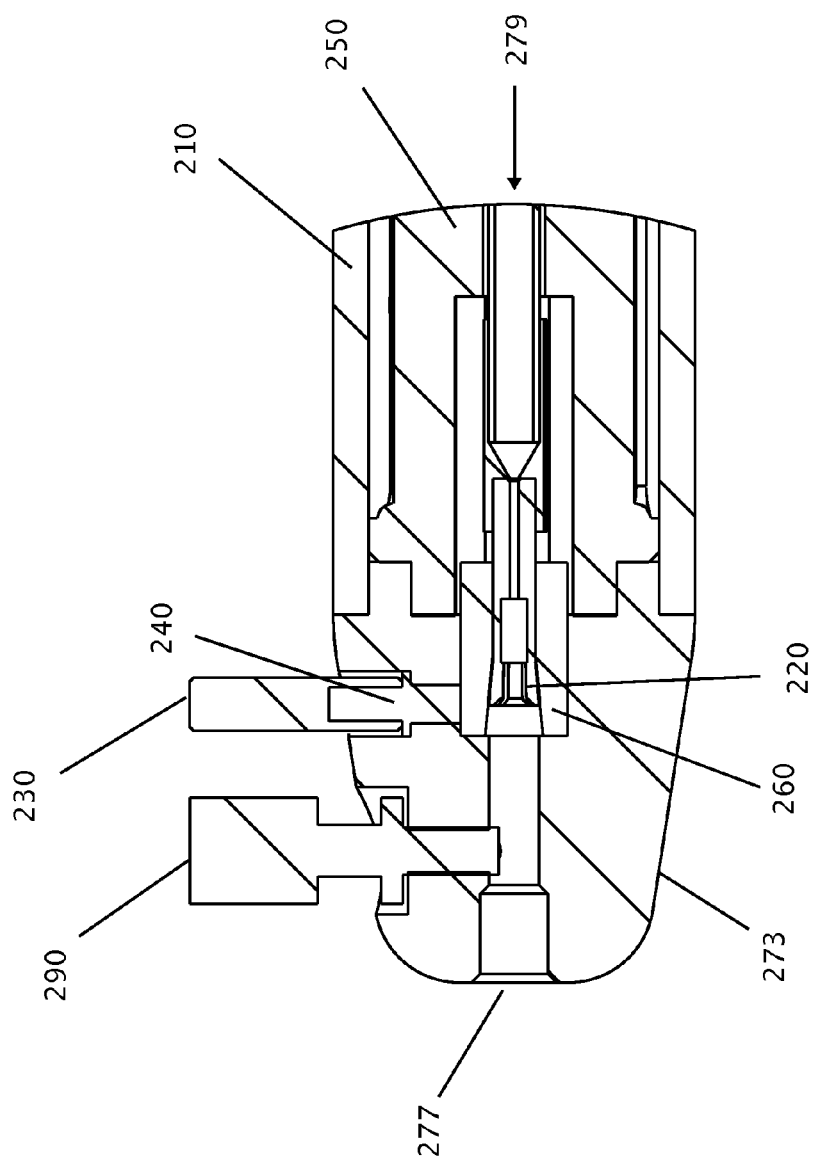
FIG. 12 is a blow-up of a cross sectional view of the distal end of cardiac pacemaker electrode mapping and attachment.
Figure 13:
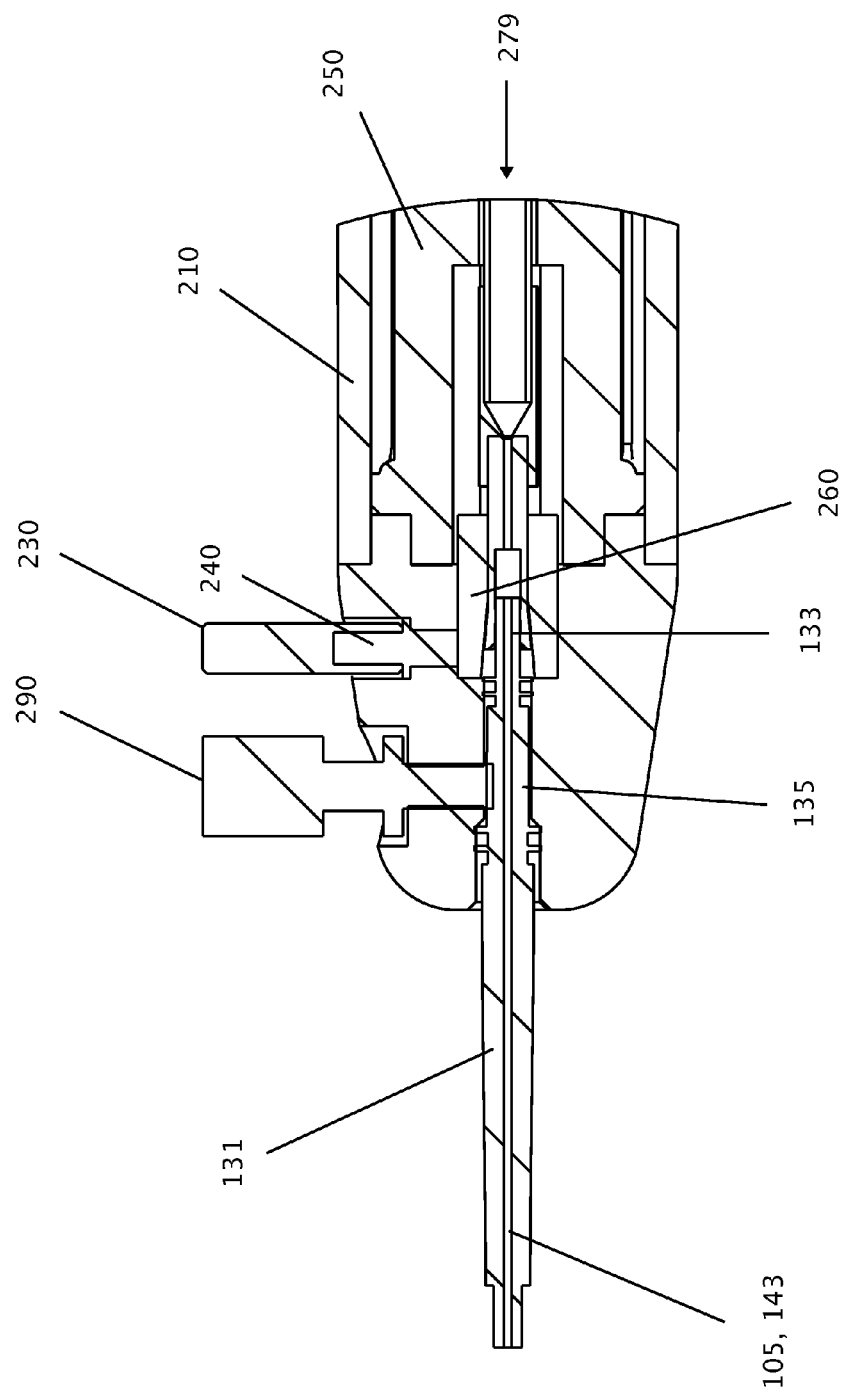
FIG. 13 is a blow-up of a cross sectional view of the distal end of electric potential mapping and electrode attachment device with attached electrode.

Electrode collar 127 is located on the distal surface of electrode 121. See FIG. 3. Electrode collar 127 is typically the outer ring on the distal surface of the electrode 121. Electrode collar 127 functions to make an electrical connection to heart tissue. Helix 122 is a corkscrew shaped screw capable of being inserted into heart tissue by screw means. Helix 122 typically has more rounded bends rather than sharp cornered bends as depicted in FIG. 3. Helix 122 has a tip 123 that may be used to puncture heart tissue in order to retrieve a proper electrical reading or to start the screw attachment means. Helix 122 also functions to make an electrical connection to heart tissue.

Wire lead 103 includes a catheter, cannula, or tube 105 running longitudinally along the full length of wire lead 103, where one end of cannula 105 leads to electrode 21 and the other end to the electromechanical connector 131, where cannula 105 extends through electromechanical connector. Cannula 105 is sized to accept a specific stylet 141 where they are typically designed in pairs, where stylet 141 is a rigid or semi-rigid wire used to guide, move, and position electrode 121 inside a body cavity.

Stylet 141 comprises and guide wire 143 and a wrench 145. 143 and 145 are rigidly connected so that each rotates along with the other. The whole structure of 141 is also known as a guide-wire. In order to use stylet 141, guide wire 143 must be completely inserted into cannula 105 and seated onto the proximal end of electrode 121. Guide wire 143 may be pre-formed in various shapes such as straight or J-shaped in order to allow easier positioning and attaching of electrode 121.

Typically, electromechanical connector 131 is an "IS-1 pacemaker connector". IS-1 pacemaker connector comprises two electromechanical connectors: 133 and 135. Electromechanical connector 133 is electrically connected to electrode collar 127 and electromechanical connector 135 is electrically connected to helix 122. Electromechanical connectors 133 and 135 are each mechanically connected to different structure on electrode 121 and each may be rotated relative to the other, thereby rotating different structure on electrode 121, relative to the other. With rotational screw electrodes, either stylet 141 or electromechanical connector 133 or both must be rotated in order to extend helix 122 from the center of electrode collar 127. Alternately, with fixed screw electrodes, either stylet 141 or electromechanical connector 133 or both must be rotated in order to start helix 122 to screw into heart tissue. There are many specifically designed electrodes 121 on the market; however, practically all include an IS-1 pacemaker connector at their proximal end, where each design has its own specifically designed stylet 141 or set of such that may be used for a specific purposes such as attaching fixed screw or rotational screw electrodes of other function.

This invention is first to provide continuously viable electrical connections between connectors 133 and 135 with concurrent ability to rotate such independently from each other, thereby yielding the ability to produce a high-quality electrocardiogram of the HIS bundle electric potential with continuous viable electric potential readings during the complete process of mapping, rotating of electrode or helix or both, screw attachment to heart tissue, and afterwards.

Pacemakers typically function by inserting stimulation electrode 121 into the superior vena cava, through the tricuspid valve 17 and rest it on the ventricle muscle, as described in Thompson. Wire lead 103 and electrode 121 must pass through catheter 101 for body insertion. This is not optimal because wire lead passes through the tricuspid valve and thus may interfere with the valve or cause an irritation. Pacemakers are intended to remain in place permanently, thus lead 103 may have long-term effects or otherwise cause damage to the valve and inefficiency of its operation. Also, the electrical stimulation of the right ventricle 9 also has long-term adverse effects on the muscle. To avoid these issues and to have better pacing, the pacing electrode should be placed and anchored into the HIS bundle 71 (or alternately anchored to septum wall 13) so that the pacing electrode is electrically connected to HIS bundle 71.

The His bundle tissue appears to lie in a small fossa at the apex of the membranous septum, where mapping is required in order to find HIS bundle 70. Mapping is the process of positioning the electrode 121, recording an electrical potential reading, repositioning the electrode 121, recording another electrical signal, and repeating until an accurate enough map or sufficient amount of electrical readings is taken by the surgeon to render an electrical topography of the heart chamber or otherwise enough information to determine the exact position on the His bundle to attach the electrode in order to stimulate the simultaneous contraction of both ventricles in order to achieve maximum efficiency. The electrical potential reading used in the mapping process is the electric potential difference between electrode collar 127 and helix tip 123. The electric potential has maximum amplitude when the electrode 121 is closest to the HIS bundle center, with the tip of the helix 123 located exactly on center of the His bundle.

As noted in Deshmukh, successful mapping requires a high-quality electrocardiogram of the HIS bundle electric potential that must be recorded and monitored by electrode 121. Electric potential mapping and electrode attachment device may be used to easily map the heart chamber in order to determine the optimal precise position for electrode 121. Electrode 121 is moved by manipulating the electric potential mapping and electrode attachment device 200 where 200 is also used as a continuous interface between the recording system (not shown) and the electrode 121 as the movement occurs.

Electric potential mapping and electrode attachment device comprises a main cylinder 210 and a secondary cylinder 250, wherein said cylinders are concentric and mounted on a common longitudinal center axis with said secondary cylinder 250 fitting completely inside of said main cylinder 210. Common longitudinal axis is void or hollow in order to receive the stylet 141, which must extend there through, where proper function requires that stylet 141 be threaded down the center of electric potential mapping and electrode attachment device as depicted. Typically, electrode lead 103 is attached first and then stylet 141 is threaded through electric potential mapping and electrode attachment device and electrode lead 103.

There are at least two openings 211 in main cylinder 210, through which said secondary cylinder 250 may be easily rotated by finger or hand within the main cylinder 210 and independently from main cylinder 210. Openings 211 are sized to be slightly larger than an average human thumbprint. Openings 211 are oval shaped in best mode. Secondary cylinder 250 has at least two ridges or other raised areas 251 on its exterior surface to provide for increased grip or friction during finger rotation of 250 within 210. Best mode 250 has eight ridges 251.

Electric potential mapping and electrode attachment device further comprises a proximal end button 271 and a distal end cap 273. Proximal end button 271 is generally cylindrical with outer diameter slightly smaller than the inner diameter of main cylinder 210. End button 271 is placed concentrically within cylinder 210 so that button 271 can slide longitudinally within cylinder 210. Proximal end of cylinder 210 has a reduced diameter end or rounded end, which acts to contain button 271 within cylinder 210. Sliding action of end button 271 within cylinder 210 is retained on the other end by spring 280. Distal cap 273 functions to provide a distal member or end of cylinder 210. Distal cap 273 is rigidly attached to cylinder 210.

Members 210, 220, 250, 260, 271, and 273 have a center passage or void 279 for receiving a catheter with electrode where the void runs from a centerpiece net 275 to a centerpiece outlet 277. In other words, electric potential mapping and electrode attachment device effective hollow at its longitudinal core with void 279, which is required so that a laparoscopic device, such as an electrode with lead, can be inserted through electric potential mapping and electrode attachment device for mapping, electrode attachment, or other procedure.

When electric potential mapping and electrode attachment device is properly connected to electromechanical connector 131 of the pacemaker, main cylinder 210 is electrically and mechanically connected to electromechanical connector 135 on lead 103. Electric potential mapping and electrode attachment device further comprises a main cylinder-to-electrode lead electromechanical connection means where there is a rigid connection and electrical connection between main cylinder 210 and lead connector 135. Said means may be by threaded member, clamping member, collet member, chuck member, magnetic member, electromagnetic member, or similar. Electrical connection of said means may be accessed at an electrical connector 290 on the electric potential mapping and electrode attachment device. Electrical connector 290 provides the ability to connect an electrical connector such as an alligator clip or similar to it while also allowing the ability to move it and slightly rotate wire lead 103, which would be adjusted in the usual way to manipulate electrode 121. Electrical connector 290 provides continuous viable electrical connection to helix 122 during rotation of helix or electrode or both.

When electric potential mapping and electrode attachment device is properly connected to electromechanical connector 131 of the pacemaker, secondary cylinder 250 is electrically and mechanically connected to electromechanical connector 133 on lead 103. Electric potential mapping and electrode attachment device further comprises: a secondary cylinder to-electrode lead mechanical connection means and a secondary cylinder to-electrode lead resilient electrical connection, where there is a rigid mechanical connection and electrical connection between main cylinder 210 and lead connector 135. This electrical connection may be accessed at an electrical connector 230 on the electric potential mapping and electrode attachment device. Electrical connector 230 provides the ability to connect an electrical connector such as an alligator clip or similar to it in order to provide a continuous viable electrical connection to said electrode collar 127, while also allowing complete rotation of electromechanical connector 133 relative to electromechanical connector 135, as is required to attach electrode 121 to heart tissue by screw means with some electrode designs, where rotation is accomplished by rotating said secondary cylinder 250.

Secondary cylinder to-electrode lead mechanical connection means may be by threaded member, clamping member, collet member, chuck member, magnetic member, electromagnetic member, or similar. In best mode, secondary cylinder-to-electrode lead mechanical connection means comprises: a collet or chuck 220 and a collet striker 260. In best mode, secondary cylinder to-electrode lead resilient electrical connection comprises a resilient electrical connector 240. This structure is used to attach electric potential mapping and electrode attachment device to electromechanical connector 133. Collet 220 is a chuck collar with at least two fingers 221 on its distal end. Collet 220 forms a collar around the electromechanical connector 133 and exerts a strong clamping force on 133 when it is tightened on such via the collet striker 260. When collet 220 is at rest, spring 280 forces collet 220 in the proximal direction into a taper section of collet striker 260. Collet striker 260 is a specifically sized and shaped bushing with distally facing taper on its interior diameter that acts to force collet fingers 221 closed. Clamping force is provided by spring 280. Spring 280 is compressed between spring retainer ring 283 and proximal end button 271. Ring 283 is fixed while button 271 slides to compress and release spring 280. Collet fingers 221 are released when end button 271 is depressed, which forces collet 220 in the distal direction, where the taper on the collet striker widens, allowing collet fingers 221 to open, thereby releasing electromechanical connector 133. Fingers 221 naturally spring open from its shape. Collet 220 is typically made of metal. Collet 220 may have 2-20 fingers 221.

Collet 220 further comprises a nut area 223 in rigid connection with the collet fingers 221. Collet is oblong shaped with fingers 221 on one end and nut area 223 on the other end or alternately in the middle of oblong shape. Nut area 223 engages counterpart structure or wrench structure on the secondary cylinder 250. Nut area 223 fits within inverse matching structure on the interior surface of secondary cylinder 250, so that cylinder 250 acts as a wrench to rotate said nut area 223 on collet, thereby rotating collet fingers 221, thereby rotating electromechanical connector 133 on the pacemaker, when the electric potential mapping and electrode attachment device is properly connected to such. Thus, connector 133 may be rotated by rotating secondary cylinder 250 when electric potential mapping and electrode attachment device is properly attached to 133.

Continuous viable electrical connection may be maintained by a resilient electrical connector 240. Resilient electrical connector 240 is resilient in that it may be compressed and it will naturally spring back into shape from the compression. Resilient electrical connector 240 is also capable of maintaining electrical conductivity during said compression and response. Resilient electrical connector 240 electrically connects collet striker 260 to said electrical connector 230 and is physically placed between such. Resilient electrical connector 240 keeps a preload positive force or pressure on collet striker 260, directed radially inward towards the center axis of the electric potential mapping and electrode attachment device, thereby allowing 240 to remain in contact with 200 as 200 is repeatedly and completely rotated. Thus, 240 must be compressed before installing between collet 220 and connector 230.

Collet striker 260 maintains electrical connection with collet 220 because collet striker 260 is clamping down on collet 220. Likewise, collet 220 maintains electrical connection with electromechanical connector 133 because collet 220 is clamping down on connector 133.

In best mode, resilient electrical connector 240 is a ball detent. Ball detent comprises a metal sphere, sliding within a hollow metal cylinder with one open end and one closed end, against the pressure of a spring. When elements are sized appropriately, conductivity between the ball and cylinder is maintained during sliding. The spring pushes the ball against the open end of the cylinder where it is retained within such because the open end of cylinder has a smaller diameter than the ball. When elements are sized appropriately, the ball rides along the surface of the collet, where 240 maintains electrical conductivity with such despite imperfections in outer circumference of collet, alignment of members, wear of members, or other imperfection. The flexible conductive range of this device would depend on the diameter of the ball, where larger diameters yield large flexible conductive ranges.

Electrical connector 290 is electrically and mechanically connected to electromechanical connector 135. In best mode connector 290 has a threaded base 291 so that one end is a threaded member 291, which can be mated with a taped hole in main cylinder 210. After the electric potential mapping and electrode attachment device is properly connected to electromechanical connector 135 on the pacemaker, connector 290 may then be connected by simply screwing in down onto 135.

After electrode attachment, a programming module or the control module may be electrically connected to connectors 290 and 230 along with the previously mentioned electrical connectors used for mapping, thereby allowing continuous electrical readings throughout programming and other control process.

What is claimed is:

1. A electric potential mapping and electrode attachment device comprising:
    an outer cylinder;
    an inner cylinder;
    a first electrical connection located on the outer surface of said outer cylinder;
    a second electrical connection located on the outer surface of said outer cylinder;
    a inner cylinder-to-electrode lead mechanical connection means;
    a inner cylinder-to-electrode lead resilient electrical connection; and
    a outer cylinder-to-electrode lead electromechanical connection means;
    wherein,
        said outer and inner cylinders are mounted concentrically to each other on a common longitudinal center axis with said inner cylinder fitting completely inside of said outer cylinder so that each cylinder may be rotated relative to the other and said common longitudinal axis is void or hollow and sized to accept by threading there through a certain laparoscopic device,
        said outer cylinder has at least one void or hole through which said inner cylinder may be rotated by thumb or finger relative to said outer cylinder;
        said inner cylinder-to-electrode lead mechanical connection means provides a reversible rigid mechanical connection between said inner cylinder and a first contact on the electrode lead so that rotation of said inner cylinder causes rotation of the first contact on electrode lead,
        said inner cylinder-to-electrode lead resilient electrical connection electrically connects said first electrical connection to the first contact on electrode lead wherein said inner cylinder-to-electrode lead mechanical connection means maintains electrical connectivity with the first contact on electrode lead when mechanically connected to such, said resilient electrical connection means electrically connects said inner cylinder-to-electrode lead mechanical connection means to said first electrical connection and maintains such electrical connection during repeated and complete rotation of said inner cylinder-to-electrode lead mechanical connection means, where said resilient electrical connection is a resilient, flexible, or plastic connection that remains electrically conductive to maintain electrical and physical contact between said first electrical connection and said inner cylinder-to-electrode lead mechanical connection means, and
        said outer cylinder-to-electrode lead electromechanical connection means mechanically and rigidly connects said outer cylinder to a second contact on the electrode lead and also electrically connects said second electrical connection to the second contact on electrode lead.

2. A electric potential mapping and electrode attachment device as recited in claim 1, wherein said inner cylinder-to-electrode lead mechanical connection means further comprises:
- a collet or chuck member;
- a collet striker member; and
- a spring, wherein,
    - said collet or chuck member has at least two finger members on its distal end, where said at least two fingers exert a strong clamping force on the first contact on the electrode lead when it is tightened via said collet striker and said spring,
    - said collet striker is a specifically sized and shaped bushing to mate with said collet or chuck member with a distally facing taper on its interior diameter that acts to force said at least two fingers closed, and
    - said strong clamping force is provided by said spring, which forces said at least two fingers into said taper, thereby closing said fingers around the first contact on the electrode.

3. A electric potential mapping and electrode attachment device as recited in claim 1, wherein said collet or chuck member further comprises a nut area in rigid connection with said at least two finger members where said collet or chuck member is oblong shaped with said at least two fingers at one end and said nut area at the other or at a mid-point and said nut area engages a counterpart structure, wrench structure, or inverse structure on the inner surface of said inner cylinder where said nut area fits within said counterpart structure, wrench structure, or inverse structure so that said inner cylinder acts as a wrench to rotate said nut area with rotation of said inner cylinder, thereby rotating said at least two fingers, thereby rotating the first contact on the electrode.

4. A electric potential mapping and electrode attachment device as recited in claim 1, wherein said inner cylinder-to-electrode lead resilient electrical connection further comprises:
- an electrically conductive sphere;
- an electrically conductive hollow metal cylinder with one open end and one closed end; and
- an electrically conductive spring, wherein,
    - said electrically conductive hollow metal cylinder extends partially through said outer cylinder with said closed end on the exterior and said open end on the interior of said outer cylinder,
    - said electrically conductive spring is placed inside said electrically conductive hollow metal cylinder at the closed end and said electrically conductive sphere is placed inside said electrically conductive hollow metal cylinder at the open end so that said electrically conductive spring forces said electrically conductive sphere against said open end of said electrically conductive hollow metal cylinder where said electrically conductive sphere is retained within said electrically conductive hollow metal cylinder because said open end has a smaller diameter than that of said electrically conductive sphere ball, and
    - said electrically conductive sphere rides along the outer surface of said collet or chuck member and maintains electrical conductivity with such despite imperfections in outer circumference of said collet or chuck member, alignment of members, or wear of members.

5. A electric potential mapping and electrode attachment device as recited in claim 1, wherein said outer cylinder-to-electrode lead electromechanical connection means comprises an oblong shaped electrically conductive member with male threads on one end that mate with a tapped hole in said outer cylinder where said oblong shaped electrically conductive member may be mechanically tightened or screwed down onto the second contact on the electrode lead to provide a rigid connection between said outer cylinder and the second contact on the electrode that is also electronically conductive connection between these members.

6. A method of using said electric potential mapping and electrode attachment device, comprising:
- a) obtaining said electric potential mapping and electrode attachment device;
- b) obtaining an electrode stylet set with an electrode member and a stylet member wherein said electrode member includes an electrode attached to a hollow wire lead and said stylet member is appropriately sized and shaped to laparoscopically navigate said electrode to, from, and within a targeted body cavity of a human or animal;
- c) threading or inserting the distal end of said stylet member through said hollow longitudinal axis of said cylinder members;
- d) threading or inserting the distal end of said stylet member through said hollow wire lead until said the distal end of stylet is seated onto the proximal end of said electrode;
- e) connecting and seating said electric potential mapping and electrode attachment device to said hollow wire lead;
- f) laparoscopically inserting said electrode to a certain position inside said targeted body cavity;
- g) recording an electric potential reading at said certain position taken from said electrode;
- h) laparoscopically moving said electrode to another certain position inside said targeted body cavity; and
- i) recording another electric potential reading at said another certain position taken from said electrode.

7. A method of using said electric potential mapping and electrode attachment device as recited in claim 6, further comprising the repeating of steps h through i as required in order to retrieve enough electric potential readings in order to render a sufficiently detailed electrical potential topography of the targeted body cavity.

8. A method of using said electric potential mapping and electrode attachment device as recited in claim 7, further comprising:
- determining an optimal placement position of said electrode within the targeted body cavity based on said detailed electrical potential topography of the targeted body cavity;
- laparoscopically moving said electrode to said optimal placement position;
- rotating said electrode in order to attach by screwing means said electrode to said optimal placement position; and
- continuously monitoring electric potential readings during said rotating.

9. A method of using said electric potential mapping and electrode attachment device as recited in claim 8, further comprising:
- reverse rotating said electrode in order to remove by unscrewing means said electrode;
- laparoscopically moving said electrode even closer to said optimal placement position;
- rotating said electrode in order to re-attach by screwing means said electrode to said optimal placement position; and
- continuously monitoring electric potential readings during said reverse rotating and said rotating.

10. A method of using said electric potential mapping and electrode attachment device as recited in claim 6, 7, 8, or 9, further comprising:

electrically connecting a programming device or a control unit device to said first and second electrical connections; and continuously monitoring electric potential readings before, during, and after said connection.

* * * * *